United States Patent [19]

Wright

[11] 3,941,781

[45] Mar. 2, 1976

[54] PREPARATION OF 3-ALKYLTHIOMETHYL CEPHALOSPORINS

[75] Inventor: Ian G. Wright, Greenwood, Ind.

[73] Assignee: Eli Lilly and Company, Indianapolis, Ind.

[22] Filed: Oct. 23, 1973

[21] Appl. No.: 408,352

Related U.S. Application Data

[63] Continuation-in-part of Ser. No. 211,692, Dec. 23, 1971, abandoned.

[52] U.S. Cl. .......... 260/243 C; 260/239.1; 424/246; 424/271
[51] Int. Cl.² ........................................ C07D 501/04
[58] Field of Search ................................ 260/243 C

[56] References Cited
UNITED STATES PATENTS 3,830,808   8/1974   Clark et al. .................... 260/243 C

*Primary Examiner*—Richard J. Gallagher
*Assistant Examiner*—Mary C. Vaughn
*Attorney, Agent, or Firm*—William C. Martens, Jr.; Everet F. Smith

[57] ABSTRACT

This invention is addressed to a new and improved method for the preparation of 3-alkylthiomethyl-7-acylamido cephalosporins in which a 3-alkanoyloxymethyl-7-acylamido cephalosporin is reacted with an alkane thiol in aqueous medium in the presence of certain inorganic salts to produce the desired 3-alkylthiomethyl product in significantly improved yields.

14 Claims, No Drawings

PREPARATION OF 3-ALKYLTHIOMETHYL CEPHALOSPORINS

This is a continuation-in-part of copending application Ser. No. 211,692, filed Dec. 23, 1971, now abandoned.

This invention relates to the preparation of cephalosporin antibiotics, and more particularly to a new and improved process for the preparation of 3-alkylthiomethyl cephalosporins.

One of the first classes of antibiotics to be discovered were the penicillins which are now well known as containing the "penam" nucleus, a thiazolidine ring with a fused beta-lactam. "Penam" nomenclature for the penicillins is described by Sheehan, Henery-Logan and Johnson in the *Journal of the American Chemical Society*, (JACS), 75, 3292, footnote 2 (1953). In accordance with this system of nomenclature, "penam" refers to the following saturated ring system:

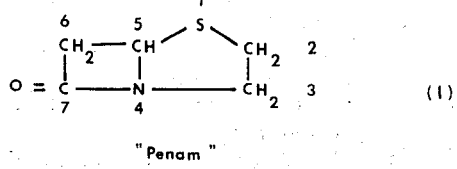

"Penam"

A more recent discovery in the field of antibiotics are the cephalosporins, which are somewhat related to the penicillins from the standpoint of chemical structure. The "penam" nomenclature system described above has been adapted to the cephalosporins by Morin, Jackson, Flynn and Roeske [JACS, 84, 3400 (1962)] who describe "cepham" as referring to the following system:

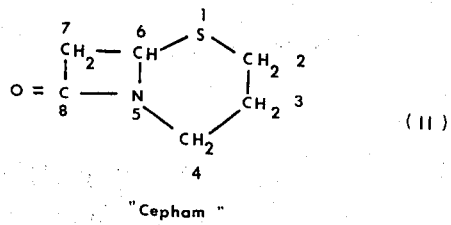

"Cepham"

"Cepham" refers to the cepham ring stucture containing a double bond, the position of which is indicated by a prefix "$\Delta$" with a superscript denoting the lowest numbered carbon atom to which the double bond is connected or by the word "delta" with the same number relationship.

In Belgian Pat. Nos. 734,532 and 734,533, description is made of certain 3-alkylthiomethyl cephalosporins having the formula:

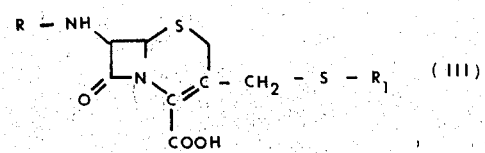

where R is an acyl group and $R_1$ is an alkyl group, which, according to the cephem nomenclature system described above, can be named 3-alkylthiomethyl-7-acylamido-$\Delta^3$-cephem-4-carboxylic acids. As is described in the aforementioned Belgian patents, the compounds (III) are prepared by reacting the corresponding 3-acetoxymethyl-7-acylamido-$\Delta^3$-cephem-4-carboxylic acid with an alkane thiol whereby the acetoxy group attached to the 3-methylene group is replaced by the corresponding alkylthio group. This reaction can be illustrated by the following equation.

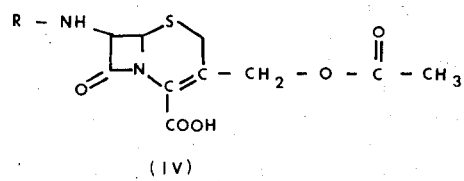

One of the primary difficulties incurred with the foregoing reaction is that the desired 3-alkylthiomethyl product is obtained in low yields, frequently of the order of only 30% or lower. Thus, the process is disadvantageous from an economic standpoint.

It is accordingly an object of the present invention to provide a new and improved process for the preparation of 3-alkyl thiomethyl-7-acylamido cephalosporins by reaction of the corresponding 3-alkanoyloxymethyl-7-acylamido cephalosporins with alkane thiols in significantly improved yields.

It has been found in accordance with the concepts of the present invention that the yield of the desired 3-alkylthiomethyl product can be significantly increased by carrying out the reaction in the presence of certain inorganic salts, such as bromides, iodides, nitrates, sulfates, thio cyanates, etc., and particularly iodide ions, in aqueous media. The presence of the salts has been found to result in an increase in yield of the desired product by a factor as high as 2 or more.

As indicated above, the reaction is carried out in aqueous media and, therefore, use is preferably made of highly water soluble iodides of the alkali metals (e.g., lithium, sodium, potassium, etc.), the alkaline earth metals (e.g., calcium, barium, etc.) or of ammonium. However, as will be appreciated by those skilled in the art, a number of other water soluble salts in the form of the bromides, iodides, nitrates, sulfates, and thiocyanates of the metals of Groups 1 and II of the Periodic Table or ammonium can also be used.

The salt chosen should not be one that itself causes destruction of cephalosporin or reacts with alkane thiols in a destructive manner. For example, salts giving aqueous solutions with a pH above 9.0 or a pH below 2.0 would generally be less desirable because degradation of cephalosporins is rapid at such extremes of pH. Similarly, various transition metal ions are known to catalyze $\beta$-lactam ring opening and are consequently to be avoided. Inorganic salts capable of oxidizing alkane thiols to disulfides or other products and salts known to react with thiol compounds to yield insoluble complexes are similarly to be avoided.

Without limiting the present invention as to theory or to any mechanism, the effect of the salt appears to be due to a combination of factors, depending on the particular cations and anions involved. Stabilization of an ionic cephalosporin intermediate by the presence of suitable counter ions may be important. Salts which have a beneficial effect appear to increase the solubility of cephalosporins and alkane thiols in the reaction medium. The beneficial effect of the preferred salts, the iodides, may be rationalized on the theory of hard and soft acids and bases.

The quantity of the source of halide ions employed is not critical and can be varied within wide ranges. In general, use should be made of an amount of the source of halide ion per part by weight of the cephalosporin starting material from 1 part by weight per part by weight of the cephalosporin starting material up to an amount sufficient to saturate the aqueous reaction medium at the reaction temperature with best results generally being achieved when the reaction medium is saturated with the salt.

The conditions employed for reaction are similarly not critical and can be varied within wide ranges. For example, use can be made of a reaction temperature within the range of 30° to 100°C, with higher reaction temperatures favoring a more rapid rate of reaction. The relative proportions of cephalosporin starting material to alkane thiol should be at least stoichiometric proportions. However, it is generally preferred to make use of an excess of alkane thiol to insure as complete a reaction as possible. For this purpose, a mole ratio of alkane thiol to cephalosporin starting material of 2 to 10 or higher may be used as desired.

As the alkane thiol, use is preferably made of alkane thiols containing 1 to 6 carbon atoms, as represented by methane thiol, ethane thiol, propane thiol, isopropane thiol, butane thiol, pentane thiol, etc.

As the cephalosporin starting material, use is made of a 3-alkanoyloxymethyl-7-acylamido cephalosporin. The preferred starting materials for use in the process of this invention are the compounds of the formula:

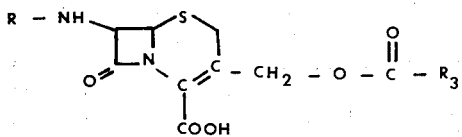

where R is an acyl group and $R_3$ is $C_1$ to $C_3$ alkyl (e.g., methyl, ethyl, propyl, etc.).

The preferred acyl groups include acyl groups having the formula

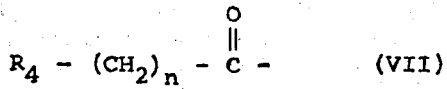

wherein n is zero or an integer from 1 to 6 and $R_4$ is a heterocyclic group in which the hetero atom is O, S, N or any combination thereof, including dioxanyl, 2-furyl, 3-furyl, imidazolyl, morpholinyl, oxazolyl, pyranyl, pyrazinyl, pyrazolyl, N-pyridyl, 2-pyridyl, 3-pyridyl, pyrimidyl, N-pyrryl, 2-pyrryl, 3-pyrryl, thiazolyl, 2-thienyl, 3-thienyl, 2-benzothienyl, 3-benzothienyl, triazinyl, triazolyl and the like; the partially and completely hydrogenated derivatives of the foregoing, such as tetrahydrofuryl, imidazolinyl, imidazolidyl, piperidyl, tetrahydropyrimidyl, pyrrolidyl and the like; as well as all of the foregoing groups which are substituted by one or more substituents including, for example, an amino or a protected amino group (e.g., a tert-butoxycarbonyl protecting group), a cyano group, a nitro group and a hydroxy group, as represented by the picolyls, methylfuryls, methyl thienyls, nitrofuryl, cyanofuryl, nitrobenzothienyl, nitropyridyl, cyanopyridyl, methoxypyrimidyl, trifluoromethyl pyridyl as well as others of the type as described in Flynn U.S. Pat. No. 3,218,318.

Illustrative of acyl groups when $R_4$ is heterocyclic are dioxanylacetyl, 2-furylcarbonyl, beta-pyrazinylpropionyl, 2-pyridylacetyl, 3-pyridylcarbonyl, 2-thienylacetyl, 3-benzothienylcarbonyl, piperidylacetyl, pyrrolidylcarbonyl, nitrobenzothienylacetyl, beta-(nitrofuryl)-propionyl, cyanopyridylcarbonyl, etc.

$R_4$ can also be a cycloalkyl group containing 4–8 carbon atoms, including cyclobutyl, cyclopentyl, cyclohexyl, cycloheptyl, etc. Illustrative of such acyl groups include cyclopentanoyl, cyclohexanoyl, 3-methylcyclohexanoyl, cyclobutylcarbonyl cyclopentylacetyl, beta-cyclopentylpropionyl, etc.

R can further be an acyl group having the general formula

wherein $R_5$ is either hydrogen or alkyl containing 1 to 8 carbon atoms (e.g., methyl, ethyl, isopropyl, n-butyl, tert-butyl, hexyl, isooctyl, etc.). Illustrative of such acyl groups are formyl, acetyl, propionyl, butyryl, isobutyryl, pentanoyl, etc.

In addition to the hydrogen and alkyl groups described above, $R_5$ can also be a group of the formula

where Q is hydrogen or one or more substituents including an amino group, a protected amino group, a cyano group, a nitro group, a $C_1$ to $C_3$ alkyl group, a halogen group, a trifluoromethyl group, a $C_1$ to $C_3$ alkoxy group, etc., and y is zero or an integer from 1 to 6; or a group of the formula

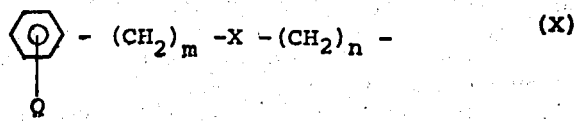

where Q is as defined above, m and n are each zero or integers from 1 to 4 and X is either O or S.

Illustrative of the resulting acyl groups where $R_5$ is one of the groups defined above are benzoyl, p-methoxybenzoyl, cyanobenzoyl, phenylacetyl, gamma-phenylbutyryl, 2,5-dimethylphenylacetyl, p-cyanophenylacetyl, beta-nitrophenylpropionyl, hydroxyphenylacetyl, m-bromobenzoyl, 3-trifluoromethylphenylacetyl, 3-tert-butoxyacetamidophenylacetyl, phenoxyacetyl, phenoxypropionyl, 3-cyanophenoxyacetyl, benzyloxycarbonyl, benzyloxyacetyl, phenoxycarbonyl, acetamidophenoxyacetyl, phenylmercaptocarbonyl, phenylmercaptoacetyl, 3-nitrophenylmercaptopropionyl, phenylethylmercaptoacetyl, trifluoromethylphenylmercaptobutyryl, as well as a variety of others.

Also included within the scope of the present invention are 7-acylamido cephalosporins in which R is an acyl group of the formula

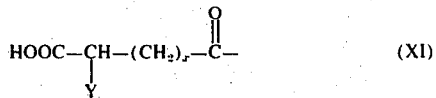

where Y is an amino group or a protected amino group, as represented by an enamine group or an acylamido group (e.g., acetamido, chloroacetamido, propionamido, etc.), and x is an integer from 1 to 5 and preferably 3 since the resulting acyl group when x is three is the valeroyl group characteristic of cephalosporin C. Preferred acyl groups of this type include 5-carboxy-5-aminovaleroyl, 5-carboxy-5-acetamidovaleroyl, 5-carboxy-5-chloroacetamidovaleroyl, 5-carboxyl-5-propionamidovaleroyl, etc.

In addition, R can be an acyl group of the formula

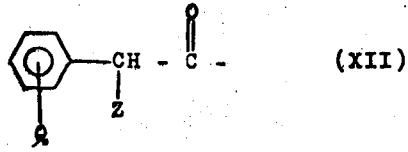

wherein Q is as defined above and Z is a protected amino as defined above, —OH, —OR$_7$, —COOH or —COOR$_8$ wherein R$_7$ is, e.g., C$_1$ to C$_6$-alkyl, trityl, benzhydryl or C$_1$ to C$_6$-alkanoyloxy, and R$_8$ is, e.g., a C$_1$ to C$_6$-alkyl such as tert-butyl. Representative of the acyl groups defined by (XII) are 2-phenyl-2-tert-butoxycarbonamidoacetyl, 2-phenyl-2-acetamidoacetyl, 2-phenyl-2-chloroacetamidoacetyl, 2-(4'-methoxyphenyl)-2-acetamidoacetyl, 2-(4'-cyanophenyl)-2-tert-butoxycarbonamidoacetyl, etc.

As will be appreciated by those skilled in the art, a number of other acyl groups may be employed in accordance with the practice of the invention, particularly those described in the aforementioned Belgian patents.

It has been found that the concepts of this invention are likewise applicable to the cephalosporin antibiotics described in copending applications, Ser. Nos. 60,556, filed Aug. 3, 1970, and 62,390, filed August 10, 1970, which have the structures:

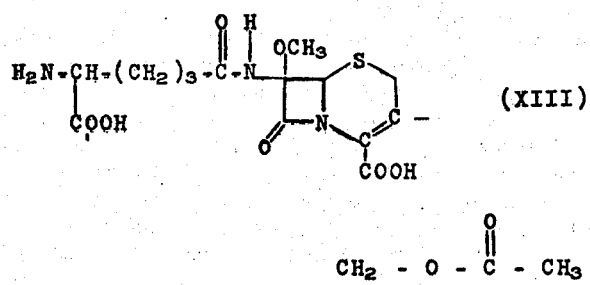

and

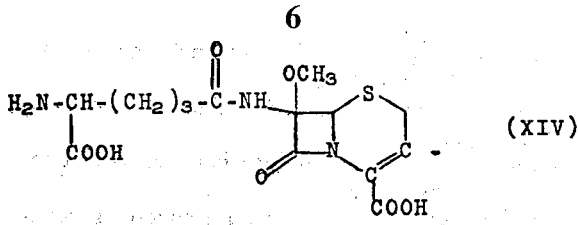

respectively, and which can be named 7-(5'-carboxy-5'-aminovaleramido)-7-methoxy-3-acetoxymethyl-Δ$^3$-cephem-4-carboxylic acid, and 7-(5'-carboxy-5'-aminovaleramido)-7-methoxy-3-carbamoyloxymethyl-Δ$^3$-cephem-4-carboxylic acid, respectively, as well as the known antibiotic:

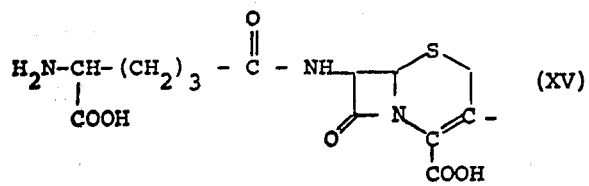

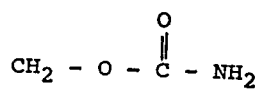

7-(5'-carboxy-5'-aminovaleramido)-3-carbamoyloxymethyl-Δ$^3$-cephem-4-carboxylic acid.

When use is made of the foregoing as starting materials in the process of this invention to prepare the corresponding 3-alkylthiomethyl compound, it may be desirable to insure that the amino group is protected by a suitable group, and preferably an acyl group (e.g., an acetyl, chloroacetyl, propionyl, tertbutoxy-carbonyl group, etc.)

Thus, the starting materials useful in accordance with this concept of this invention have the formula:

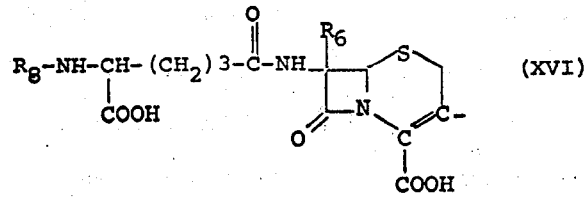

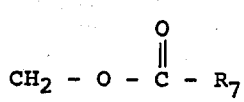

where R$_6$ is H or methoxy, R$_7$ is CH$_3$ or NH$_2$, provided that where R$_6$ is H, R$_7$ is NH$_2$, and R$_8$ is an acyl protecting group. The reaction conditions employed in this concept of the invention are the same as those described.

Since the reaction between the cephalosporin starting material and the alkane thiol is carried out in aqueous medium, it is generally preferred that the cephalosporin starting material be employed in the form of a water-soluble salt, such as the alkali metal salts or ammonium salts, or the salt formed with an organic base, such as quinoline or the like.

Representative of the 3-alkanoyloxymethyl-7-acylamido cephalosporin starting material which can be employed in the practice of the present invention are the following compounds.

3-propionoxymethyl 7-(2'-thienylacetamido-Δ³-cephem-4-carboxylic acid 3-acetoxymethyl 7-(2'-furylamido)-Δ³-cephem-4-carboxylic acid 3-acetoxymethyl 7-(2'furylpropionamido)-Δ³-cephem-4-carboxylic acid 3-butyryloxymethyl 7-(2'-furylacetamido)-Δ³-cephem-4-carboxylic acid 3-acetoxymethyl 7-(3'-thienylacetamido)-Δ³-cephem-4-carboxylic acid 3-acetoxymethyl 7-(3'-methyl-2'-thienylacetamido)-Δ³-cephem-4-carboxylic acid 3-acetoxymethyl 7-(1'-pyrazoleacetamido)-Δ³-cephem-4-carboxylic 3-acetoxymethyl 7-(N'-methyl-2'-pyrrylacetamido)-Δ³-cephem-4-carboxylic acid 3-propionoxymethyl 7-(5'-imidazolinylacetamido)-Δ³-cephem-4-carboxylic acid 3-acetoxymethyl 7-(2'-piperidylacetamido)-Δ³-cephem-4-carboxylic acid 3-acetoxymethyl 7-(3'-bromo-2'-pyridylacetamido)-Δ³-cephem-4-carboxylic acid 3-acetoxymethyl 7-(2'-thienylpropionamido)-Δ³-cephem-4-carboxylic acid 3-acetoxymethyl 7-(5'-methoxy-3'-pyridylacetamido)-Δ³-cephem-4-carboxylic acid 3-acetoxymethyl 7-(cyclopentylacetamido)-Δ³-cephem-4-carboxylic acid 3-propionoxymethyl 7-cyclohexylpropionamido-Δ³-cephem-4-carboxylic acid 3-propionoxymethyl 7-acetamido-Δ³-cephem-4-carboxylic acid 3-acetoxymethyl 7-isobutyrylamido-Δ³-cephem-4-carboxylic acid 3-butyryloxymethyl 7-formamido-Δ³-cephem-4-carboxylic acid 3-acetoxymethyl 7-(5'-carboxy-5'-acetamidoaleramido)-Δ³-cephem-4-carboxylic acid 3-acetoxymethyl 7-(2'-phenyl-2'-acetamidoacetamido)-Δ³-cephem-4-carboxylic acid The starting materials of the present invention can be prepared by any of a number of methods known to those skilled in the art. For example, use can be made of the procedures described in U.S. Pat. No. 3,218,318 to Flynn and the procedures described in copending applications, Ser. No. 72,236, filed Sept. 14, 1970, by Charles F. Murphy and Ser. No. 94,988, filed Dec. 3, 1970, by Stjepan P. Kukolja.

As will be appreciated by those skilled in the art, in some cases, the 7-acylamido group may contain functional groupings which are reactive with the alkane thiol. For example, when use is made of 3-acetoxymethyl 7-(5'-carboxy-5'-chloroacetamidovaleramido)-Δ³-cephem-4-carboxylic acid, the reaction proceeds as follows:

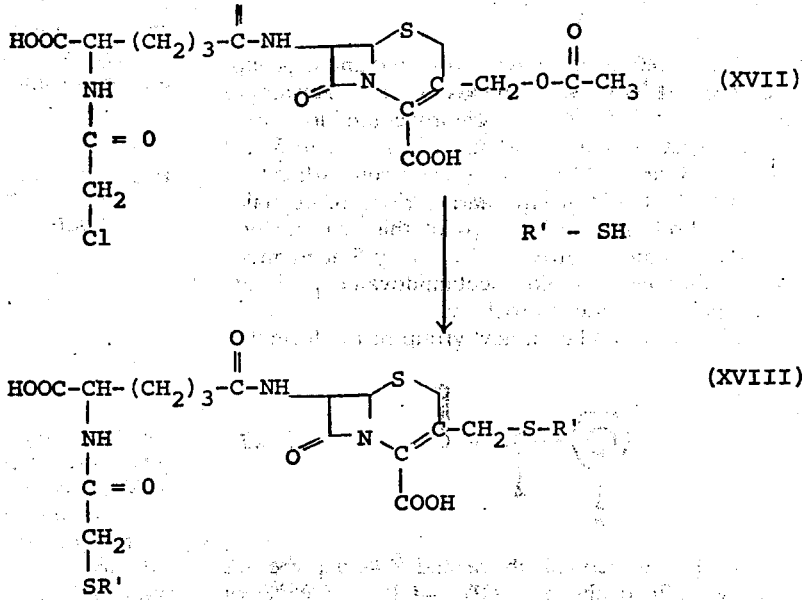

However, this is not disadvantageous since it is contemplated that the 7-acylamido group may be cleaved in accordance with known procedures, such as by the method of Chauvette in copending application Ser. No. 651,662, filed July 7, 1967, to form the corresponding 3-alkylthiomethyl-7-amino compound which can be reacylated to provide the desired 7-acylamido group in a known manner.

Having described the basic concept of the present invention, reference is now made to the following examples which are provided by way of illustration, and not by way of limitation of the practice of the process of this invention.

EXAMPLE 1

A sample of 47.1 g (150 m.moles) of 3-acetoxymethyl-7-acetamido-Δ³-cephem-4-carboxylic acid was dissolved in 150 ml (150 m.moles) of a 1 Normal solution of sodium hydroxide in a 500 ml Parr pressure bottle, and the resulting solution was cooled to −15° in a bath of ice and methanol. Thereafter, 250 g of potassium iodide were added to the reaction mixture and the bottle was evacuated to remove dissolved gases from the solution. Then, 30 ml (540 mMoles) of methane thiol from a cylinder was condensed in a graduated cylinder in a dry ice-acetone bath, and the condensed thiol was added to the cooled reaction mixture.

The bottle was then sealed and placed in a water bath at a temperature of about 80° and the reaction mixture stirred vigorously at 70° ± 2° for 1.75 hours, after which it was cooled in a bath of ice and methanol for 15 minutes and the bottle opened. Excess methane thiol was removed in vacuo for 15 minutes, and the resulting aqueous solution was extracted with ethyl acetate three times, using 500 ml of the ethyl acetate.

The ethyl acetate extracts were then washed with saturated sodium bicarbonate solution, and the combined aqueous layers were acidified to a pH of 1.5. The acidified solution was extracted with ethyl acetate, and the product separated and identified as 3-methylthiomethyl-7-acetamido-$\Delta^3$-cephem-4-carboxylic acid. 31.6 g of product mp 178-179° dec were removed constituting a yield of 70%. ir(mull) 3280, 1770, 1710, 1610, 1520 cm$^{-1}$; uv max (MeOH) 265 nm ($\epsilon$9,000); nmr (CDCl$_3$ + DMSOd$_6$) $\delta$2.07 (6H,s), 3.46 (1H, d, J=13.5Hz), 3.60 (2H,s), 3.85 (1H, d, J=13.5Hz), 5.04 (1H, d, J=5Hz), 5.71 (1H, d/d, J=5Hz, J=8.5Hz), 8.28(1H, d, J=8.5Hz), 9.41 (1H, broad s).

Anal. Calcd. for $C_{11}H_{14}N_2O_4S_2$: C, 43.71; H, 4.67; N, 9.27; S, 21.21. Found: C, 43.97; H, 4.92: N, 9.03; S, 21.06.

The procedure described above was repeated under essentially the same conditions except that no potassium iodide was added to the reaction mixture. The same product was obtained in a yield of 31%.

EXAMPLE 2

Using the procedure described in Example 1, 40 mMoles of 3-acetoxymethyl-7-acetamido-$\Delta^3$-cephem-4-carboxylic acid was reacted with 140 mMoles of methanethiol using a variety of salts.

The results are tabulated below:

| Salt | Amount of Salt (g) | Yield |
|---|---|---|
| KBr | 40 | 40% |
| NaI | 75 | 66% |
| NaBr | 50 | 52% |
| Ca(NO$_3$)$_2$.4H$_2$O | 80 | 58% |
| Mg(NO$_3$)$_2$.6H$_2$O | 80 | 44% |
| BaI$_2$.2H$_2$O | 70 | 66% |
| CaI$_2$.nH$_2$O | 70 | 59% |
| LiI | 70 | 68% |
| NH$_4$I | 70 | 59% |
| K$_2$SO$_4$ | 70 | 46% |

As is evident from the foregoing, a good yield of the desired 3-methylthiomethyl product was obtained with each of the salts.

EXAMPLE 3

A sample of 8.36 g (20 mMoles) of the sodium salt of cephalothin [3-acetoxymethyl-7-(2'-thienylacetamido)-$\Delta_3$-cephem-4-carboxylic acid] was dissolved in 50 ml of water in a 500 ml Parr pressure bottle. 75 g of potassium iodide were added and the resulting solution was cooled to a temperature of −10° in a bath of ice and methanol and a vacuum applied to remove dissolved gases. Thereafter, 6 ml (about 108 mMoles) of methanethiol was condensed in a graduated cylinder and added to the reaction bottle, which was then promptly sealed and placed in a water bath, initially at 80°, and the contents were stirred at 70°±2° for four hours.

The reaction bottle was then cooled to −10° before opening, and a vacuum was applied for 15 minutes to remove excess methanethiol. The resulting aqueous solution was extracted three times with 150 ml of ethyl acetate, which was washed two times with a cold sodium bicarbonate solution. The combined aqueous layers were acidified to a pH of 2 with dilute HCl, and the product extracted three times with ethyl acetate. The ethyl acetate solution was treated with sodium sulfate, filtered and evaporated to dryness in vacuum yielding 7.6 g of a crude acidic fraction. Pure 3-methylthiomethyl-7-(2'-thienylacetamido)-$\Delta_3$-cephem-4-carboxylic acid crystallized from an ethyl acetate solution (m.p. 148°-150° dec. 4.94 g, 64% yield): ir (CHCl$_3$) 3320, 1780, 1710, 1680, 1505 cm$^{-1}$; uv max (EtoH) 236 nm ($\epsilon$ 14,300), 266 (8,900); nmr (CDCl$_3$ × DMSOd$_6$)$\delta$2.04 (3H, s), 3.44 (1H, d, J= 13Hz), 3.58 (2H, s), 3.80 (2H, s); 3.84 (1H, d, J=13Hz), 5.03 (1H, d, J=5Hz), 5.66 (1H, d/d, J=5, 8.5Hz), 6.96 (2H,m), 7.22 (1H, m), 8.87 (1H, d, J=8.5Hz), 10.8 (1H, very broad).

Anal. calcd. for $C_{15}H_{16}N_2O_4S_3$: C, 46.86; H, 4.19; N, 9.29; S. 25.02. Found: C, 46.81; H, 4.38; N, 7.13: S, 24.96.

The procedure described was repeated under essentially the same conditions, but without addition of potassium iodide. 6.6 g of the crude fraction were obtained which yielded, upon crystalization, 2.67 g of the desired 3-methylthiomethyl product (yield of 35%).

EXAMPLE 4

A sample of 30 g (100 mMoles) of 3-acetoxymethyl-7-formamido-$\Delta^3$-cephem-4-carboxylic acid was dissolved in 100 ml (100 mMoles) of a 1 Normal sodium hydroxide solution. The solution was treated with 170 g of potassium iodide and 19 ml (344 mMoles) of methanethiol using the procedure described in Example 1. The reaction was carried out at a temperature of about 70° for 1.7 hours. The product, 3-methylthiomethyl-7-formamido-$\Delta^3$-cephem-4-carboxylic acid, was obtained in a yield of 74% (21.4 g). Nmr spectrum showed no trace of unchanged starting material.

EXAMPLE 5

A sample 46.59 g of the monoquinoline salt of 3-acetoxymethyl-7-(5'-chloroacetamido-5'-carboxyvaleramido)-$\Delta^3$-cephem-4-carboxylic acid (purity 79.9%, 60 mMoles) was suspended in 100 ml of water containing 225 g of potassium iodide. The solution was then treated with 25 g (520 mMoles) of methanethiol according to the procedure described in Example 1. The reaction was carried out for 2 hours and 40 minutes at about 70°. The product, 3-methylthiomethyl-7-(5'-methylthioacetamido-5'-carboxyvaleramido)-$\Delta^3$-cephem-4-carboxylic acid, was isolated in good yield as in Example 1 except that 10% ethanol in ethyl acetate was the extraction solvent. The nmr spectrum of the product showed no trace of starting material: nmr (DMSOd$_6$), 1.62 (4H, m), 1.98 (3H, s), 2.11 (3H, s), 2.21 (2H, m), 3.13 (2H, s), 3.52 (1H, d, J=14Hz), 3.62 (2H, s), 3.72 (1H, d, J=14Hz), 4.20 (1H, m), 5.12 (1H, d, J=5Hz), 5.61 (1H, d/d, J=5Hz), 8.20(1H, d, J=8Hz), 8.83 (1H, d, J=8Hz).

EXAMPLE 6

The procedure described in Example 1 is repeated using ethane thiol in place of the methane thiol. The reaction is carried out at 70°C. for 2 hours, and the product is removed by the procedure described in Example 1.

The product, 3-ethylthiomethyl 7-acetamido-$\Delta^3$-cephem-4-carboxylic acid, is obtained in comparable yields.

EXAMPLE 7

The procedure described in Example 6 is repeated using potassium bromide as the halide salt. Again, good yields of the 3-ethylthiomethyl product are obtained.

EXAMPLE 8

In this example 3-acetoxymethyl 7-(2'-triazinylacetamido)-$\Delta^3$-cephem-4-carboxylic acid is reacted with propane thiol in accordance with the procedure described in Example 6. The product, 3-propylthiomethyl 7-(2'-triazinylacetamido-3-cephem4-carboxylic acid, is obtained in good yield.

EXAMPLE 9

A sample of 3-acetoxymethyl 7-(2'-phenyl-2'-acetamidoacetamido)-$\Delta^3$-cephem-4-carboxylic acid is reacted with methane thiol in the presence of sodium iodide. The 3-methylthiomethyl 7-(2'-phenyl-2'-acetamidoacetamido-$\Delta^3$-cephem-4-carboxylic acid is obtained in good yield.

EXAMPLE 10

In this example, 3-propionoxymethyl 7-(5'-nitro-2'-thienylacetamido-$\Delta^3$-cephem-4-carboxylic acid is reacted with ethane thiol in the presence of sodium bromide. The product is 3-ethylthiomethyl 7-(5'-nitro-2'-thienylacetamido)-$\Delta^3$-cephem-4-carboxylic acid, and is obtained in good yield.

EXAMPLE 11

Using the procedure described in Example 6, 3-acetoxymethyl 7-(2'-morpholinylacetamido)-$\Delta^3$-cephem-4-carboxylic acid is reacted with butane thiol in the presence of potassium bromide. The corresponding 3-butylthiomethyl 7-(2'-morpholinylacetamido)-$\Delta^3$-cephem-4-carboxylic acid is obtained in good yield.

EXAMPLE 12

In this example, the procedure of Example 1 is repeated using 3-acetoxymethyl 7-(2'-phenyl-2'-chloroacetamidoacetamido)-$\Delta^3$-cephem-4-carboxylic acid and methane thiol in the presence of sodium bromide. The corresponding 3-methylthiomethyl 7-(2'-chloroacetamidoacetamido)-$\Delta^3$-cephem-4-carboxylic acid is obtained in good yield.

EXAMPLE 13

The monoquinoline salt of 3-acetoxymethyl-7-(5'-propionamido -5'-carboxyvaleramido)-$\Delta^3$-cephem-4-carboxylic acid (purity 85%, 35.32, 50 mMoles) was suspended in a cold solvent of KI (160 gm) in water (70 ml), $CH_3SH$ was added and the reaction mixture heated at 70° for 1.75 hours as in Examples 1. Workup as in Example 5 gave a 67% yield of 3-methylthiomethyl-7-(5'-propionamido-5'-carboxyvaleramido)-$\Delta^3$-cephem-4-carboxylic acid, identified by its nmr spectrum: nmr ($DMSOd_6$)$\delta$0.98 (3H, t, J=7.5Hz), 1.60 (4H), 1.98 (3H, s), 2.13 (2H, q. J=7.5Hz), 2.20 (2H), 3.51, 3.71 (2H, AB, J=13.5Hz), 3.62 (2H, s), 4.18 (1H), 5.14 (1H, d, J=5Hz), 5.59 (1 H, d/d, J=5Hz, J=8.5Hz), 7.96 (1H, d. J=7.5Hz), 8.81 (1H, d, J=8.5Hz).

When the same reaction was carried out with no salt present, the product was a mixture of the methylthiomethyl product and starting material. The yield of the methylthiomethyl compound was estimated at about 35%.

EXAMPLE 14

3-Acetoxymethyl-7-phenoxyacetamido-$\Delta^3$-cephem-4-carboxylic acid, potassium salt (17.78 g, 40 mMoles) was dissolved in a cold solvent of KI (70 gm) in $H_2O$ (40 ml), in a Párr pressure bottle. $CH_3SH$ (12 ml) was added, the bottle was sealed and heated at 70° for one hour and 50 minutes. The acidic product was isolated as in Example 1, and treated with diphenyldiazomethane to form the benzhydryl ester, which was purified by chromatography on silica gel. The product, diphenylmethyl 3-methylthiomethyl-7-phenoxyacetamido-$\Delta^3$-cephem-4carboxylate (5.82 g, 26% yield), was identified by its nmr spectrum: nmr ($CDCl_3$)$\delta$1.85 (3H, s), 3.45 (1H, d, J=14Hz), 3.51 (2H, s), 3.65 (1H, d, J=14Hz), 4.55 (2H, s), 5.03 (1H, d, J=5Hz), 5.86 (1H, d/d, J=5Hz, J=9Hz), 6.8-7.6 (17H, m).

When exactly the same reaction was carried out with not KI present, only a 14% yield of the product was obtained.

EXAMPLE 15

The effect of salt concentration on the reaction yield was established by the series of experiments summarized in the following table. The experiments were carried out by the procedure of Example 1.

| Reaction Scale mMoles | Amount $CH_3SH$ mMoles | Volume $H_2O$ ml | Amount KI g | Time Hrs. & Min. | Temp. °C Fraction | Total Acidic Product | Yield Crystalline | m.p. |
|---|---|---|---|---|---|---|---|---|
| 20 | 130 | 20 | 50 | 1:45 | 70–72 | 79.8% | 68.6% | 172–174° |
| 20 | 130 | 20 | 20 | 1:45 | 72 | 82.0% | 56.0% | 175–177° |
| 20 | 130 | 20 | 10 | 1:55 | 67–72 | 87.0% | 51.1% | 174–176° |
| 20 | 130 | 20 | 5 | 1:45 | 72 | 83.8% | 42.6% | 174–175° |
| 40 | 140 | 40 | 0 | 1:45 | 70–72 | 76.9% | 31.0% | 169–170° |

EXAMPLE 16

Using the procedure described in Example 6, 7-benzamido-3-propionoxymethyl-$\Delta^3$-cephem-4-carboxylic acid is reacted with methane thiol in the presence of potassium iodide. The product, 7-benzamido-3-methylthiomethyl-$\Delta^3$-cephem-4-carboxylic acid, is obtained in good yield.

EXAMPLE 17

Again, using the procedure described in Example 6, 7-phenylmercaptoacetamido-3-acetoxymethyl-$\Delta^3$-cephem-4-carboxylic acid is reacted with ethane thiol in the presence of sodium iodide. The 3-ethylthioethyl product is obtained in good yield.

EXAMPLE 18

In this example, 7-(5'-carboxy-5'-propionamidovaleramido)7-methoxy-3-acetoxymethyl-$\Delta^3$-cephem-4-carboxylic acid is reacted with methane thiol in the presence of potassium iodide in accordance with the procedure described in Example 6. The 3-methylthiomethyl product, 7-(5'-carboxy-5'-propionamidovaleramido)-7-methoxy-3-methylthiomethyl-$\Delta^3$-cephem-4-carboxylic acid is obtained in good yield.

EXAMPLE 19

Using the procedure described in Example 6, 7-(5'-carboxy5'-acetamidovaleramido)-7-methoxy-3-carbamoyloxymethyl-$\Delta^3$-cephem4-carboxylic acid is reacted with ethane thiol in the presence of sodium bromide. 7(5'-carboxy-5'-acetamidovaleramido)-7-methoxy-3-ethylthiomethyl-$\Delta^3$-cephem-4-carboxylic acid is obtained as product in good yield.

EXAMPLE 20

The sodium salt of Cephalosporin C (8.77 g, 20 mMoles) dissolved in water (20 ml) containing KI (50 gm) in a 500 ml Parr bottle, was treated with $CH_3SH$ (8 ml, about 140 mMole) at 70° for 2 hours as described previously. The aqueous reaction mixture was washed with ethyl acetate to remove neutral material and then passed through a column of Pittsburgh 12 × 40 carbon (vol. 1000 ml). Elution of the column with water (4 l.) removed potassium iodide. The cephalosporin was recoverd by eluting with 50% water/acetone (4 l.), concentrating the eluate in vacuo to remove acetone and lyophilizing the aqueous residue. The solid product was taken up in a little water and crystallized by diluting with acetone and scratching. The product, 7-(5-amino-5-carboxyvaleramido)-3-methylthiomethyl-$\Delta^3$-cephem-4-carboxylic acid, potassium salt (4.67 g., 53%) was identified spectrally, especially by nmr: $\delta(D_2O)$ 1.82 (4H,m), 2.11 ( 3H, s), 2.41 (2H, t, J=6.5Hz), 3.34, 3.75 (2H, AB, J=14Hz), 3.39, 3.76 (2H, AB, J=18Hz), 3.75 (1H, t, J=5Hz), 5.14 (1H, d, J=5Hz), 5.59 (1H, d, J=5Hz).

EXAMPLE 21

The sodium salt of 7-(5'-amino-5'carboxyvaleramido)-7-methoxy-3-acetoxymethyl-$\Delta^3$-cephem-4-carboxylic acid (1.0 g, 2.19 mMoles) was treated with 1 ml of methane thiol in a solution containing 4.5 g of KI and 2.2 ml of water in a 15 ml pressure vessel at 70°C for 2 hours. The product was isolated (as in Example 20) by absorption onto a carbon column (volume of 125 ml), washing (with 800 ml $H_2O$) to remove salt and elution with 50 percent aqueous acetone (1 liter).

The product obtained was 7-(5'-amino-5'-carboxyvaleramido)-7-methoxy-3-(methylthiomethyl)-$\Delta^3$-cephem-4-carboxylic acid, potassium salt, in a yield of 50.5 percent. The product was identified spectrally, especially by nmr. $\delta(D_2O)$ 1.88 (4H, m), 2.02 (3H, s), 2.50 (2H, m), 3.34, 3.74 (2H, AB q J=18 Hz), 3.35, 3.71 (2 H, AB q, J=14Hz), 3.56 (3H, s), 3.77 (1H, t, J=6Hz), 5.23 (1H, s).

It will be apparent that various changes and modifications may be made in the details of formulation, procedure and use without departing from the spirit of the invention, especially as defined in the following claims.

Temperatures herein are in °C.

I claim:

1. In a process for the preparation of 3-alkylthiomethyl-7-acylamido cephalosporins in which a 3-alkanoyloxymethyl-7-acylamido cephalosporin is reacted with an alkane thiol containing 1-6 carbon atoms, the improvement comprising carrying out the reaction in aqueous medium in the presence of an effective amount of an inorganic salt selected from the group consisting of the highly water soluble iodide, bromide, thiocyanate, nitrate and sulfate salts of the metals of Groups I and II and ammonium iodide to increase the yield of the 3-alkylthiomethyl-7-acylamido cephalosporin.

2. A process as defined in claim 1 wherein the salt is a salt of the alkali metals and alkaline earth metals.

3. A process as defined in claim 1 wherein the salt is an iodide or bromide.

4. A process as defined in claim 1 wherein the salt is selected from the group consisting of alkali metal and ammonium iodides.

5. A process as defined in claim 1 wherein the salt is potassium iodide.

6. A process as defined in claim 1 wherein the salt constitutes at least 1 part by weight per part by weight of the 3-alkanoyloxymethyl-7-acylamido cephalosporin.

7. A process as defined in claim 1 wherein the salt is present in an amount sufficient to substantially saturate the aqueous medium at the reaction temperature.

8. A process as defined in claim 1 wherein the cephalosporin has the formula

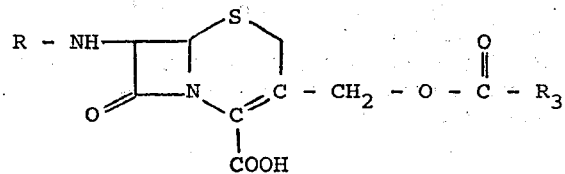

where R is an acyl group and $R_3$ is $C_1$ to $C_3$ alkyl.

9. A process as defined in claim 8 where R is selected from the group consisting of an acyl group of the formula

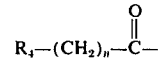

wherein $R_4$ is selected from the group consisting of a heterocyclic group in which the hetero atom is selected from the group consisting of S, N, O and combinations thereof and a cycloalkyl group containing 4 to 8 carbon atoms, and n is zero or an integer from 1 to 6; an acyl group of the formula

wherein $R_5$ is selected from the group consisting of hydrogen, $C_1$ to $C_8$ alkyl, a group of the formula

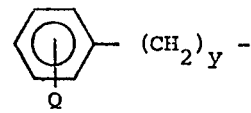

wherein Q is hydrogen or a substituent and y is zero or an integer from 1 to 6, and a group of the formula

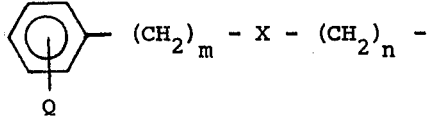

wherein Q is as defined above, m and n are each zero or integers from 1 to 4 and X is O or S; an acyl group of the formula

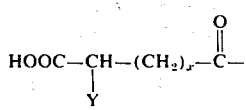

wherein Y is an amino or a protected amino group and x is an integer from 1 to 5; and an acyl group of the formula

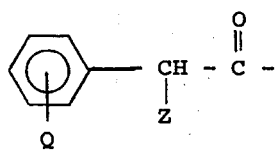

wherein Q is as defined above and Z is protected amino, —OH, —OR$_7$, —COOH or —COOR$_8$ where R$_7$ is C$_1$ to C$_6$ alkyl, trityl, benzhydryl or C$_1$ to C$_6$ alkanoyloxy, and R$_8$ is C$_1$ to C$_6$ alkyl.

10. A process for the preparation of 3-alkylthiomethyl cephalosporins comprising reacting a cephalosporin of the formula

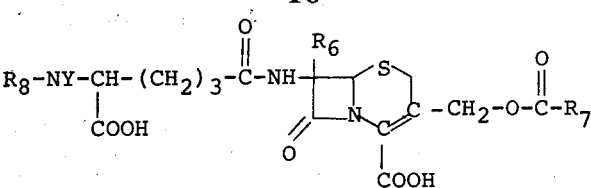

R$_6$ is selected from the group consisting of hydrogen and methoxy and R$_7$ is selected from the group consisting of methyl and amino, provided that where R$_6$ is hydrogen, R$_7$ is amino, and R$_8$ is hydrogen or an acyl protecting group, with an alkane thiol containing 1-6 carbon atoms in aqueous medium in the presence of an effective amount of highly water soluble iodide, bromide, thiocyanate, nitrate and sulfate salts of the metals selected from the group consisting of Groups I and II and ammonium iodide to increase the yield of the 3-alkylthiomethyl-7-acylamido cephalosporin.

11. A process as defined in claim 10 wherein the salt is a salt of the alkali and alkaline earth metals.

12. A process as defined in claim 10 wherein the salt is an iodide or bromide.

13. A process as defined in claim 10 wherein the salt is selected from the group consisting of alkali metal and ammonium iodides.

14. A process as defined in claim 10 wherein the salt is present in an amount sufficient to substantially saturate the aqueous medium at the reaction temperature.

* * * * *